US00PP13579P2

(12) United States Plant Patent
Hofmann

(10) Patent No.: US PP13,579 P2
(45) Date of Patent: Feb. 18, 2003

(54) NEW GUINEA IMPATIENS PLANT NAMED 'FISNICS LIGHT PINK'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 09/998,607

(22) Filed: Nov. 30, 2001

(51) Int. Cl.[7] ..... A01H 5/00

(52) U.S. Cl. ..... Plt./318

(58) Field of Search ..... Plt./318

(56) References Cited

PUBLICATIONS

UPOV–ROM GTITM Computer Database 2002/03, GTI Jouve Retrieval Software, Citation for Impatiens 'Fisnics Light Pink'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of New Guinea Impatiens plant named 'Fisnics Light Pink', characterized by its outwardly spreading, rounded and uniformly mounded plant habit; freely branching and freely flowering habit; large rounded light pink-colored flowers with red purple-colored eye that are positioned above and beyond the foliage; and dark green-colored leaves.

1 Drawing Sheet

BOTANICAL CLASSIFICATION/CULTIVAR DESIGNATION

*Impatiens hawkeri* cultivar Fisnics Light Pink.

BACKGROUND OF THE INVENTION

The present Invention relates to a new and distinct cultivar of New Guinea Impatiens plant, botanically known as *Impatiens hawkeri,* and hereinafter referred to by the name 'Fisnics Light Pink'.

The new Impatiens is a product of a planned breeding program conducted by the Inventor in Hillscheid, Germany. The objective of the breeding program is to develop new Impatiens cultivars that flower relatively early with large rounded flowers and attractive flower colors.

The new Impatiens originated from a cross made by the Inventor in May, 1997 of the *Impatiens hawkeri* cultivar Kipas, disclosed in U.S. Plant Pat. No. 10,432, as the male, or pollen, parent with the *Impatiens hawkeri* cultivar Danhargrap, not patented, as the female, or seed, parent. The cultivar Fisnics Light Pink was discovered and selected by the Inventor as a flowering plant within the progeny of the stated cross in a controlled environment in Moncarapacho, Portugal in March, 1998.

Asexual reproduction of the new cultivar by terminal cuttings taken in Moncarapacho, Portugal, since March, 1998, has shown that the unique features of this new Impatiens are stable and reproduced true to type in successive generations.

SUMMARY OF THE INVENTION

The following traits have been repeatedly observed and are determined to be the unique characteristics of 'Fisnics Light Pink'. These characteristics in combination distinguish 'Fisnics Light Pink' as a new and distinct Impatiens cultivar:

1. Outwardly spreading, rounded and uniformly mounded plant habit.

2. Freely branching and freely flowering habit.

3. Large rounded light pink-colored flowers with a red purple-colored eye that are positioned above and beyond the foliage.

4. Dark green-colored leaves.

Plants of the new Impatiens can be compared to plants of the male parent, the cultivar Kipas. In side-by-side comparisons conducted by the Inventor in Hillscheid, Germany, plants of the new Impatiens differed from plants of the cultivar Kipas in the following characteristics:

1. Plants of the new Impatiens are shorter than plants of the cultivar Kipas.

2. The lower surfaces of leaves of plants of the new Impatiens are green in color whereas the lower surfaces of leaves of plants of the cultivar Kipas are red in color.

3. Flower color of plants of the new Impatiens is light pink whereas flower color of plants of the cultivar Kipas is light purple.

Plants of the new Impatiens can be compared to plants of the female parent, the cultivar Danhargrap. In side-by-side comparisons conducted by the Inventor in Hillscheid, Germany, plants of the new Impatiens differed from plants of the cultivar Danhargrap in the following characteristics:

1. Plants of the new Impatiens are not as compact as plants of the cultivar Danhargrap.

2. The lower surfaces of leave of plants of the new Impatiens are green in color whereas the lower surfaces of leaves of plants of the cultivar Danhargrap are dull red in color.

3. Flowers of plants of the new Impatiens have a distinct eye whereas flowers of plants of the cultivar Danhargrap do not have a distinct eye.

4. Flower color of plants of the new Impatiens is light pink whereas flower color of plants of the cultivar Danhargrap is red purple.

Compared to plants of the cultivar Fisnics Pink, disclosed in U.S. Plant Patent Ser. No. 09/921,482, plants of the new Impatiens have lighter pink-colored flowers and less glossy leaves.

Plants of the new Impatiens are similar to plants of the cultivar Danharpin, not patented, in flower color. However, in side-by-side comparisons conducted by the Inventor in Hillscheid, Germany, plants of the new Impatiens differed from plants of the cultivar Danharpin in the following characteristics:

1. Plants of the new Impatiens are larger and not as compact as plants of the cultivar Danharpin.

2. Leaves of plants of the new Impatiens are not as glossy as leaves of plants of the cultivar Danharpin.

3. Plants of the new Impatiens have mostly light green-colored stems whereas plants of the cultivar Danharpin have red-colored stems.

4. Plants of the new Impatiens have larger flowers than plants of the cultivar Danharpin.

5. Flowers of plants of the new Impatiens are flat whereas flowers of plants of the cultivar Danharpin are somewhat cupped.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens.

The photograph comprises a side perspective view of a typical flowering plant of 'Fisnics Light Pink' grown in a container.

DETAILED BOTANICAL DESCRIPTION

The cultivar Fisnics Light Pink has not been observed under all possible environmental conditions. The phenotype may vary somewhat with variations in environment such as temperature and light intensity, without, however, any variance in genotype.

The aforementioned photographs, following observations and measurements describe plants grown in Langley, British Columbia, Canada, under commercial practice in a greenhouse. Rooted young plants were planted in 17.5-cm containers during the spring and the following observations and measurements were taken during the summer about 17 weeks later. During the production of the plants, day temperatures ranged from 21 to 24° C. and night temperatures were about 17° C. In the following description, color references are made to The Royal Horticultural Society Colour Chart, 1995 Edition, except where general terms of ordinary dictionary significance are used.

Botanical classification: *Impatiens hawkeri* cultivar Fisnics Light Pink.

Commercial classification: New Guinea Impatiens cultivar Fisnics Light Pink.

Parentage:

*Male parent.*—*Impatiens hawkeri* cultivar Kipas, disclosed in U.S. Plant Pat. No. 10,432.

*Female parent.*—*Impatiens hawkeri* cultivar Danhargrap, not patented.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 159A in color.

Plant description:

*General appearance.*—Outwardly spreading, low, rounded and uniformly mounded plant growth habit; dense and bushy; freely branching and flowering habit.

*Crop time.*—From a rooted cutting, about 10 to 11 weeks are required to produce finished flowering plants in 12-cm containers.

*Plant height.*—About 19.35 cm.

*Plant diameter or spread.*—About 27.7 cm.

*Lateral branches.*—Quantity per plant: About 9 to 11. Length: About 18 cm. Diameter: About 6.5 mm. Internode length: About 4.25 cm. Color: Mostly light green, 143C, with weak reddish brown, 179A to 181A, anthocyanin at the nodes.

*Foliage description.*—Arrangement: Primarily in whorls. Length: About 12.5 cm. Width: About 4.1 cm. Shape: Elliptic. Apex: Acuminate. Base: Acute. Margin: Serrulate with ciliation. Texture: Smooth, not rugose; glabrous. Color: Young foliage, upper surface: 137D to 143A. Young foliage, lower surface: 138B. Mature foliage, upper surface: Between 137A and 139A. Mature foliage, lower surface: 139C. Venation, upper surface: Towards leaf base, 179B; towards leaf apex, 141D. Venation, lower surface: 141D. Petiole: Length: About 1.2 to 2 cm. Diameter: About 3.5 mm. Color: Upper surface: Close to 47C. Lower surface: 179C.

Flower description:

*Flower type and flowering habit.*—Single and large rounded light pink-colored flowers with red purple-colored eye. Freely and continuously flowering; usually about 7 to 9 flowers and flower buds per lateral branch. Flowers flat and positioned above and beyond the foliage and typically face parallel to the leaf canopy. Petals self-cleaning; gynoecium persistent. Flowers not fragrant.

*Flower longevity.*—Flowers last about 8 to 9 days on the plant.

*Flowering season.*—Year-round under greenhouse conditions; in the garden, flowering from spring until fall. Plants begin flowering about 8 to 9 weeks after planting.

*Flower buds.*—Length: About 2.5 cm. Diameter: About 1.6 cm. Shape: Ovoid. Color: 68A to 68B.

*Flower length.*—About 7.3 cm.

*Flower width.*—About 7 cm.

*Flower depth.*—About 1.2 cm.

*Petals.*—Quantity: Five per flower, imbricate. Length: Banner petal: About 3 cm. Lateral and base petals: About 3.4 cm. Width: Banner petal: About 5.4 cm. Lateral and base petals: About 3.85 cm. Shape: Cordate. Apex: Emarginate, lobed. Base: Attenuate. Margin: Entire. Aspect: Mostly flat. Texture: Smooth; satiny. Color: When opening, upper and lower surfaces: 68B. Fully opened, upper surface: 65A; center of banner petal, 68B; color fading to 65D with subsequent development; eye zone, 66B. Fully opened, lower surface: 65A.

*Spur.*—Quantity: One per flower. Length: About 6 to 7 cm. Diameter: At apex: About 0.5 mm. At flower:

About 3 mm. Aspect: Curved downward. Color: 53C.

*Peduncles.*—Length: About 5.5 to 6.5 cm. Diameter: About 2 mm. Strength: Strong, flexible. Color: 145C; overlain with anthocyanin, 47C or 53D.

*Reproductive organs.*—Androecium: Stamen number: Five fused at anthers, hooded; filaments free. Anther length: About 6.5 mm. Anther shape: Obovate. Anther color: 62B to 62C. Pollen amount: Moderate. Pollen color: 8D. Gynoecium: Pistil quantity: One per flower. Pistil length: About 5.5 mm. Stigma color: Cream, 157A. Ovary: Five-celled. Ovary color: 137C.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisnics Light Pink', as illustrated and described.

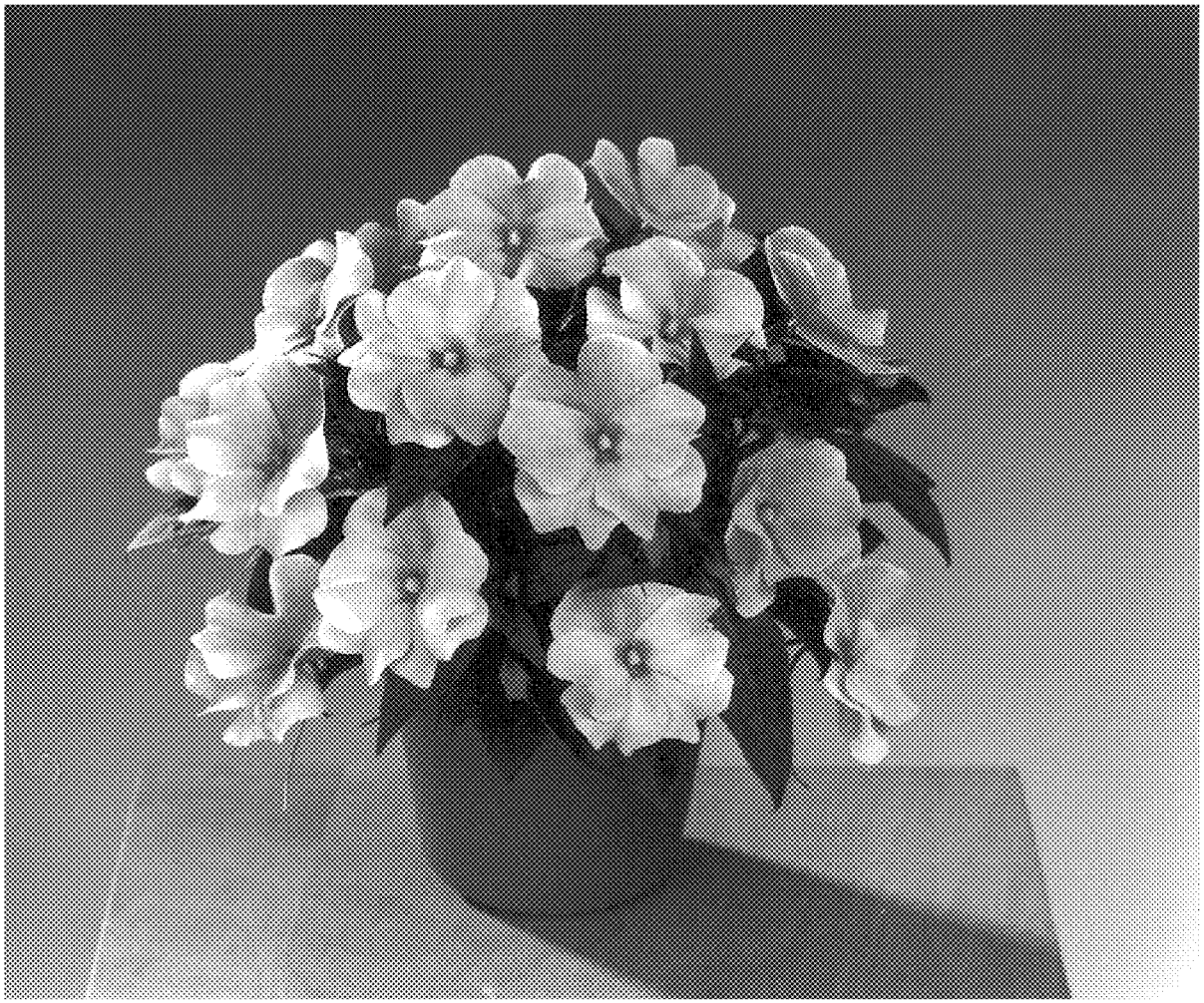

* * * * *